United States Patent [19]
Van Der Puy

[11] Patent Number: 5,880,317
[45] Date of Patent: *Mar. 9, 1999

[54] PREPARATION OF 1,1,2,3,3-PENTAFLUOROPROPANE

[75] Inventor: M. Van Der Puy, Cheektowaga, N.Y.

[73] Assignee: AlliedSignal Inc., Morristown, N.J.

[*] Notice: The portion of the term of this patent subsequent to May 24, 2011, has been disclaimed.

[21] Appl. No.: 129,879

[22] Filed: Sep. 30, 1993

[51] Int. Cl.$^6$ .............................. C07C 19/08; C07C 17/08
[52] U.S. Cl. ...................... 570/176; 570/167; 570/169; 204/157.95
[58] Field of Search ................................. 570/167, 176, 570/169; 204/157.95

[56] References Cited

U.S. PATENT DOCUMENTS

| | | | |
|---|---|---|---|
| 2,917,559 | 9/1959 | Sweeney et al. | 260/653.6 |
| 5,315,048 | 5/1994 | Van Der Puy et al. | 570/176 |

FOREIGN PATENT DOCUMENTS

| | | | |
|---|---|---|---|
| 675455 | 12/1963 | Canada | 570/167 |
| 0522639 | 1/1993 | European Pat. Off. | 570/167 |
| 0539989 | 5/1993 | European Pat. Off. | 570/176 |
| 4210653 | 7/1992 | Japan | 570/176 |
| A-101035 | 11/1965 | United Kingdom . | |

OTHER PUBLICATIONS

J. Burdon et al., "Partial Fluorination of Tetrahydrofuran with Cobalt Trifluoride", J. Chem. Soc. (C), (1969), pp. 1739–1746.

Henne et al., "The Addition of Hydrogen Fluoride to Halo–Olefins", J. Am. Chem. Soc., (1943), 65, p. 1271–1272.

Henne et al., "Perfluorinated Olefins", J. Am. Chem. Soc., (1948), 70, pp. 130–132.

O. Paleta, "Ionic Addition Reactions of Halomethanes With Fluoroolefins", Fluorine Chemistry Reviews, Ed. P. Tarrant et al, (1977), Chap. 2, pp. 39–71.

Miller, et al., "Preferential Replacement Reactions of Highly Fluorinated Alkyl Halides. Preparation . . .", J. Am. Chem. Soc., (1957), 79, pp. 4164–69.

*Primary Examiner*—Alan Siegel
*Attorney, Agent, or Firm*—Lois A. Gianneschi

[57] ABSTRACT

The present invention relates to a process for the reduction dechlorination of $ClCF_2CFClCF_2Cl$ to $HCF_2CHFCF_2H$ comprising the step of contacting 1,2,3-trichloropentafluoroethane and $H_2$ over a catalyst selected from the group consisting of palladium, platinum, ruthinium, rhodium, iridium and mixtures thereof under reaction conditions sufficent to produce a product stream containing 1,1,2,3,3-pentafluoropropane. The present invention further relates to a three step process wherein the $ClCF_2CFClCF_2Cl$ to be reduced is synthesized by:

(a) reacting HF with a compound of formula I: $XCH=CYCH_2X$, where X is H, Cl, or F, Y is H or Cl; to give a compound of formula II: $CH_2XCFYCH_2X$, where X and Y are the same as in the compound of formula I:

(b) chlorinating the compound of formula II to give a compound of formula III: $CCl_{3-m}F_mCFClCCl_{3-m}F_m$ where m is zero or 1, and (c) fluorinating the compound of formula III to give $CClF_2CFClCF_2Cl$.

A composition of matter having the formula $HCF_2CHFCF_2Cl$ is also disclosed.

18 Claims, No Drawings

PREPARATION OF 1,1,2,3,3-PENTAFLUOROPROPANE

BACKGROUND OF THE INVENTION

Hydrofluorocarbons are of great interest due to their potential to replace ozone depleting CFCs used in a variety of applications, including cleaning solvents and blowing agents. For example, 1,1,2,3,3-pentafluoropropane is a useful blowing agent or cleaning solvent (Eur. 381,986) which has been produced as a minor by-product in the cobalt trifluoride fluorination of tetrahydrofuran (J. Burdon et. al. J. Chem. Soc. (C), 1969, 1739).

The art is currently active in searching for methods to reduce chlorofluorocarbons (CFCs) to hydrofluorocarbons (HFC's), to find suitable replacements for ozone depleting CFCs. Simple alkyl halides may be readily dehalogenated via catalytic reduction in the presence of base under mild conditions. However, such dehalogenations are not suitable for the reduction of perhalogenated compounds.

Some CFCs have been reductively dechlorinated in the vapor phase in the presence of a catalyst. However, the reductive dechlorinations of the prior art suffer from a lack of selectivity and reduction control. Reductive defluorination can accompany reductive dechlorination even at relatively low temperatures. For example, EPA 435,705 (Jul. 3, 1991) discloses that the reduction of $CF_3CFCl_2$ over iridium on carbon at 150° C. gave $CF_3CHClF$ (74%) while reduction over palladium under the same conditions gave 95% $CF_3CH_3$.

Consequently, there is a need for a process to prepare 1,1,2,3,3-pentafluoropropane using a method which is both economical, and amenable to large scale manufacture.

DESCRIPTION OF THE INVENTION

The present invention relates to a process for the reductive dechlorination of $ClCF_2CFClCF_2Cl$ to $HCF_2CHFCF_2H$ comprising the step of contacting 1,2,3-trichloropentafluoropropane and $H_2$ in the presence of a catalyst selected from the group consisting of palladium, platinum, ruthenium, rhodium, iridium and mixtures thereof, under reaction conditions sufficent to produce a product stream containing 1,1,2,3,3-pentafluoropropane (HFC-245ca). The present invention further relates to a three step process wherein the PREPARATION OF 1,1,2,3,3-PENTAFLUOROPROPANE $ClCF_2CFClCF_2Cl$ to be reduced is synthesized by:

(a) reacting HF with a compound of formula I: $XCH=CYCH_2X$, where X is H, Cl, or F, Y is H or Cl; to give a compound of formula II: $CH_2XCFYCH_2X$, where X and Y are the same as in the compound of formula I:

(b) chlorinating the compound of formula II to give a compound of formula III: $CCl_{3-m}F_mCFClCCl_{3-m}F_m$ where m is zero or 1, and (c) fluorinating the compound of formula III to give $CClF_2CFClCF_2Cl$. It has been surprisingly found that when the reductive dechlorination of $ClCF_2CFClCF_2Cl$ is carried out in the presence of a catalyst selected from the group consisting of Pd, Pt, Ru, Rh, Ir and mixtures thereof, 1,1,2,3,3-pentafluoropropane is produced with very little reduction of the fluorine atoms. This result was particularly surprising in view of the fact that when $CF_3CFCl_2$ is reductively dechlorinated in the presence of a palladium catalyst at temperatures as low as 150° C., the primary product (95%) is the defluorinated compound, $CF_3CH_3$.

The catalysts of the present invention can take any form. However, powders are not preferred in vapor phase reductions because powders are small enough to be carried through the reactor or cause large pressure drops. Accordingly, the catalysts of the present invention are preferably shaped. The catalysts may be prepared in any shape, and by any technique known in the art such as extrusion or tableting. Examples of suitable shapes include, but are not limited to large chunks, spheres and pellets.

Preferably the catalyst material is Pd or Pt. The catalysts are preferably supported by an inert supporting material such as carbon granules or alumina pellets. The preferred support is carbon granules. The catalyst material may be deposited on the support in any convenient form such as a halide or oxide of the catalyst material. Typically the desired halide or oxide salt is impregnated on the support, dried then reduced to the metal with $H_2$.

The catalysts are available commercially and generally can be obtained having 0.5 to 20% by weight of the metal on the support material. More commonly, loadings of 0.5 to 5% weight percent are employed. Examples include 1% palladium on activated carbon granules and 0.5% platinum on ⅛" alumina pellets.

The reduction may be carried out in either the liquid or the vapor phase. However, for large scale production the reaction is preferably conducted in a continuous flow system by passing vapors of $ClCF_2CFClCF_2Cl$, along with hydrogen, over one of the critically defined catalysts. The reactor may be made of any corrosion resistant material such as Inconel.

Pressure is not critical. Both subatmospheric pressures or pressures up to 100 atmospheres may be used, the latter is especially useful in batch operations. Atmospheric pressures are frequently the most convenient and are thus preferred.

Useful temperatures range from about 100° C. to about 350° C. Preferred temperatures are between about 150° C. to about 250° C. These temperature ranges are particularly surprising as defluorination of the feed material $CF_3CFCl_2$ has been observed in the art in the presence of palladium at temperatures as low as 150° C., and one skilled in the art would have expected defluorination to increase with temperature.

Based on reaction stoichiometry, the required ratio of hydrogen to $CF_2ClCFClCF_2Cl$ is 3 moles hydrogen per mole of $CF_2ClCFClCF_2Cl$. The amount of hydrogen may vary from one to about ten times the stoichiometric ratio, with about two to about four times the stoichiometric amounts being preferred.

Conditions for the reduction vary and depend, in part, on the activity of the catalyst (which depends on the type of metal used, its concentration on the support, and the nature of the support material), and the contact or residence time in the reactor. Residence times may be adjusted by changing the reaction temperature, the catalyst volume, and the flow rates of hydrogen and/or organic material to be reduced. Useful contact times range from about 0.1 second to about 2 minutes. In the present case, preferred contact times range from about 3 to about 20 seconds.

In the reduction of $ClCF_2CFClCF_2Cl$ at atmospheric pressure and at temperatures of about 100° C. to about 325° C., both $HCF_2CHFCF_2H$ and $HCF_2CHFCF_2Cl$ are generally present in the reactor effluent stream. The ratio of $HCF_2CHFCF_2H$ to $HCF_2CHFCF_2Cl$ increases with increasing reaction temperature. Continuous operation at high temperatures (>300° C.) is not preferred, however, due to potential gradual loss of catalyst activity. High conversions may be achieved by increasing the contact time, or equivalently, by recyling the product stream until the desired conversion is obtained. After separating the desired HCF$_2$CHFCF$_2$H from HCF$_2$CHFCF$_2$Cl and other under-reduced materials that may be present, the HCF$_2$CHFCF$_2$Cl may be fed into the reactor again, either alone or mixed with ClCF$_2$CFClCF$_2$Cl. Alternatively, the HCF$_2$CHFCF$_2$Cl produced may be separated out and used in the production of agricultural chemicals.

The HFC-245ca may be separated from the product stream via any known separation or purification method, such as distillation.

The reduction feed material, ClCF$_2$CFClCF$_2$Cl, is not commercially available in bulk quantities. Accordingly, the present invention also includes a process for making ClCF$_2$CFClCF$_2$Cl.

In the first step of the process HF is contacted with a compound having the formula I:

XCH=CYCH$_2$X, where X is H, Cl, or F and

Y is H or Cl, in either the vapor or liquid phase.

The reaction may be carried out at temperatures between about 15° C. and about 100° C., depending on the number of halogens present in the compound of formula (I). For example, isopropyl fluoride is conveniently made by passing HF and propylene over activated carbon at 25° C. as described in U.S. Pat. No. 2,917,559. HF may also be reacted with CH$_2$=CClCH$_2$Cl at 50°–60° C. to form CH$_3$CFClCH$_2$Cl.

Examples of acceptable compounds of formula I include propylene, allyl fluoride, allyl chloride, 2,3-dichloro-1-propene, 2-chloropropene, 2-chloro-3-fluoro-1-propene, and 1,3-dichloropropene. The most preferred compounds will depend on whether a vapor or liquid phase reaction is desired. The preferred compounds, for reasons of economy and bulk availability are propylene, allyl chloride, and 2,3-dichloro-1-propene. Preferably these compounds are contacted with HF in the vapor phase. Compounds of formula I having chlorine or fluorine on the C-1 carbon ( $\underline{C}$=C—C) are less desirable as the addition of HF may take place in the reverse direction as a competing reaction. A. L. Henne and E. P. Plueddeman, J. Am Chem. Soc., 1943, 65, 1271. When the reaction is carried out in the liquid phase allyl chloride or 2,3-dichloro-1-propene is preferred.

The reaction product from step 1 has a formula II:

CH$_2$XCFYCH$_2$X, where X is H, Cl, or F and Y is H or Cl.

In the second step of the process of the present invention, the reaction product of formula II is chlorinated to give a chlorination product having the formula:

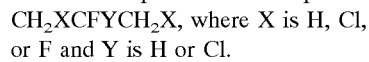  (III).

wherein m=0 or 1

The chlorination step may be carried out via any method known in the art. For example, chlorine may be bubbled into CH$_3$CFClCH$_2$Cl while irradiating with UV light at ambient pressure and temperature to give a mixture of CCl$_3$CFClCCl$_3$ and CCl$_3$CFClCC$_2$H, which yields pure CCl$_3$CFClCCl$_3$ upon distillation. A. L. Henne and T. H. Newby (J. Am. Chem. Soc., 1948, 70, 130). Thermal chlorinations may also be employed (including oxychlorination, ie. chlorination using a combination of oxygen and HCl which react to form water and chlorine).

The reaction products compounds of formula II need not be isolated in pure form prior to chlorination.

Alternatively, compositions of formula III may be produced by reacting CCl$_4$ or CFCl$_3$ with a two carbon olefin selected from the group consisting of CFCl=CF$_2$, CFCl=CFCl, CF$_2$=CFCH and CFCl=CFH. Such reactions are catalyzed by Lewis acids in a solvent selected from the group consisting of carbon tetrachloride, methylene chloride and carbon disulfide at temperatures which are generally below about 50° C. Preferred catalysts include AlCl$_3$, FeCl$_3$, BF$_3$ and BCl$_3$ with AlCl$_3$ being most preferred. 0. Paleta, "Fluorine Chemistry Reviews", Ed. P. Tarrant, M. Dekker, New York, chapter 2 (1977).

In the third step the chlorination product which may be a mixture of CCl$_3$CFClCCl$_3$ and CCl$_3$CFClCCl$_2$H, or pure CCl$_3$CFClCCl$_3$ is fluorinated. The fluorination is conducted such that the secondary chlorine is not replaced with fluorine and that the two end groups proceed with fluorination to the same degree, i.e. to —CF$_2$Cl and not —CF$_3$ or —CFCl$_2$. This can be achieved by reacting the chlorination product with HF, preferably in the presence of a catalyst such as antimony fluoride, antimony chlorofluorides and mercuric oxide for liquid phase reactions and chromium-containing solid catalysts for vapor phase reactions. For example, the fluorination of CCl$_3$CFClCCl$_3$ under pressure at about 225° C. for two hours and then overnight at 150° C. with a reagent obtained by reacting SbF$_3$ with chlorine gave CF$_2$ClCFClCF$_2$Cl. Alternatively, CF$_2$ClCFClCFCl$_2$ may be treated with HF and HgO under pressure at about 175° C. for about 24 hours to yield CF$_2$ClCFClCF$_2$Cl. It is believed that fluorination of mixtures of CFCl$_2$CFClCCl$_3$ and CFCl$_2$CFClCFCl$_2$ under similar conditions would also afford the desired ClCF$_2$CFClCF$_2$Cl.

EXAMPLE 1

The hydrogenation reactor used in this example consisted of a vertical 1 inch diameter glass tube heated with electrical heating tape. A thermocouple measured the temperature in the center of the tube. The catalyst bed consisted of 10 cc 0.5% Pd/Al$_2$O$_3$ (⅛" pellets available from Englehard or Johnson Matthey mixed with 15 cc glass helices) for a total bed volume of 25 cc. Hydrogen flow rate was 140 cc/min. Organic (ClCF$_2$CFClCF$_2$Cl) was fed into the top of the reactor via a syringe pump. Effluent from the reactor was collected in two −78° C. cold traps. The organic flow was started at an initial temperature of 156° C. The temperature increased to 186° C. over one half hour and was maintained at 185°–190° C. for 1 hour, then increased to 225° C. After a total time of 4.25 hours, 42.1 g of ClCF$_2$CFClCF$_2$Cl had been fed into the reactor. The cold traps contained 22.8 g material. Gas chromatographic analysis indicated that the recovered material contained 27% low boiling material (bp<HCF$_2$CFHCF$_2$H). The desired compound, HCF$_2$CHFCF$_2$H was present as 7% of the mixture, with the remaining 66% being chlorinated compounds.

EXAMPLE 2

The reactor described in Example 1 was charged with a catalyst consisting of 20 cc 1% palladium on carbon (4 to 8 mesh, purchased from Aldrich) mixed with 10 cc glass helices. Hydrogen flow rate was 140 cc/min. The reactor temperature was 255°–265° C. during most of the 4.5 hour run time. A total of 46.8 g ClCF$_2$CFClCF$_2$Cl was charged and 25.1 g product was collected in the cold traps. Gas chromatographic analysis of this material indicated <3% low boiling components, 39% HCF$_2$CHFCF$_2$H, 51% HCF$_2$CHFCF$_2$Cl and 7% C$_3$HCl$_2$F$_5$.

Examples 1 and 2 show that HFC-245ca may be produced in good yield with very little defluorination via reductive dechlorination in the presence of a palladium catalyst.

EXAMPLE 3

A total of 65.1 g ClCF$_2$CFClCF$_2$Cl was hydrogenated as described in Example 2 over 6 hours at 325°–330° C. to give 34.4 g crude product which was analyzed via gas chromatography and found to be comprised of 49% HCF$_2$CHFCF$_2$H.

EXAMPLE 4

A 28.3 g mixture comprised of 58.8% HCF$_2$CHFCF$_2$H and 36k HCF$_2$CHFCF$_2$Cl was hydrogenated as described in Example 2 over a period of 3 hours at an average temperature of 325° C. Crude product (22.8 g) was obtained from the cold traps which was comprised of 86.1% HCF$_2$CHFCF$_2$H and 10.1% HCF$_2$CHFCF$_2$Cl. Distillation of this material gave 95% pure HCF$_2$CHFCF$_2$H, having a boiling point of 39°–39.5° C. at 748 mm Hg. Thus, the mixture produced in Example 2 may be easily converted in very high yields to the desired product via recycling the product back through the hydrogenation reaction of the present invention.

EXAMPLE 5

In the apparatus and manner described in Example 1, 16.8 g ClCF$_2$CFClCF$_2$Cl was passed over 20 cc 0.5% Pt on carbon (4–8 mesh) during a period of 1.5 hours at an average temperature of 265° C. The hydrogen flow rate was 140 cc/min. The cold trap contained 8.3 g liquid, which, as determined by gas chromatographic analysis, consisted of 38.3% HCF$_2$CHFCF$_2$H and 2.83% HCF$_2$CHFCF$_2$Cl. Thus, reductive dechlorination in the presence of a platinum catalyst also yields HFC-245ca with little defluorination.

EXAMPLE 6

Using the procedure of W. T. Miller, Jr. and A. H. Fainberg (J. Am. Chem. Soc., 1957, 79, 4164), ClCF$_2$CFClCF$_2$Cl was dechlorinated with Zn/ZnCl in ethanol to give CF$_2$=CFCF$_2$Cl. This olefin was hydrogenated over a catalyst bed made up of 15 cc 1% Pd/C mixed with 50 cc glass rings. A total of 35.0 g of the olefin was passed over the catalyst (along with hydrogen at 140 cc/min) during 4¼ hours at an average temperature of 110° C. The cold trap contained 33.7 g liquid which consisted of 6% unreacted olefin, 17% HCF$_2$CFHCF$_2$H, and 74% HCF$_2$CHFCF$_2$Cl. Distillation gave HCF$_2$CHFCF$_2$Cl, bp 39° C. (HCF$_2$CHFCF$_2$Cl and HCF$_2$CHFCF$_2$H appeared to azeotrope at about 37°–38° C.). The NMR spectra confirmed the structural assignment and confirmed that it is the same material formed in the direct reduction of ClCF$_2$CClFCF$_2$Cl. Thus, CF$_2$ClCF=CF$_2$, made by conventional processes may be reduced to HCF$_2$CHFCF$_2$H according to the present invention.

I claim:

1. A process comprising:
   contacting, for a contact time of from about 0.1 second to about 2 minutes and at a temperature from about 100° C. to about 350° C., 1,2,3-trichloropentafluoropropane and H$_2$ over a catalyst selected from the group consisting of palladium, platinum, ruthenium, rhodium, iridium and mixtures thereof supported on carbon to produce 1,1,2,3,3-pentafluoropropane.

2. The process of claim 1 wherein said contacting step is conducted in the vapor phase.

3. The process of claim 2 wherein said catalyst is palladium.

4. The process of claim 2 wherein said catalyst is platinum.

5. The process of claim 3 wherein the temperature is from about 150° C. to about 250° C.

6. The process of claim 3 wherein said contact time ranges from about 3 to about 20 seconds.

7. The process of claim 1 additionally comprising the step of repassing at least a part of the product stream containing the 1,1,2,3,3-pentafluoropropane over the catalyst to produce more 1,1,2,3,3-pentafluoropropane.

8. A process comprising the steps of:
   reacting, under pressure and at a temperature from about 150° C. to about 225° C. a chlorinated compound having the formula (III) CCl$_{3-m}$F$_m$CFClCCl$_{3-m}$F$_m$, wherein m is 0 or 1, with HF, in the presence of a second catalyst selected from the group consisting of antimony fluoride, antimony chloride, antimony chlorofluorides, mercuric oxide and chromium containing solid catalysts, to produce 1,2,3-trichloropentafluoropropane; and
   contacting, for a contact time of from about 0.1 second to about 2 minutes and at a temperature from about 100° C. to about 350° C., the 1,2,3-trichloropentafluoropropane and H$_2$ over a catalyst selected from the group consisting of palladium, platinum, ruthenium, rhodium, iridium and mixtures thereof supported on carbon to produce 1,1,2,3,3-pentafluoropropane.

9. The process of claim 8 wherein said second catalyst is selected from the group consisting of antimony fluoride, antimony chloride, antimony chlorofluoride and mercuric oxide and the fluorination is conducted in the liquid phase.

10. The process of claim 8 wherein said second catalyst is a chromium containing solid and the fluorination is conducted in the vapor phase.

11. The process of claim 8 wherein said chlorinated compound is 1,1,1,2,3,3,3-heptachlorofluoropropane.

12. The process of claim 8 wherein said chlorinated compound is produced by reacting CCl$_4$ or CFCl3 with a two carbon olefin selected from the group consisting of CFCl=CF$_2$, CFCl=CFCl, CF$_2$=CFCH and CFCl=CFH in the presence of a Lewis acid selected from the group consisting of AlCl$_3$, FeCl$_3$, BF$_3$ and BCl$_3$ at temperatures below about 50° C.

13. The process of claim 8 wherein said chlorinated compound is produced by chlorinating a compound having the formula (II)
   CH$_2$XCFYCH$_2$X, where X is H, Cl,
   or F and Y is H or Cl.

14. The process of claim 13 wherein said chlorinating step is conducted via a method selected from the group consisting of bubbling chlorine into the chlorinated compound while irradiating with UV light, thermal chlorination and oxychlorination.

15. The process of claim 8 wherein the compound of formula (II) is produced by contacting HF with an unsaturated compound having the formula (I):
   XCH=CYCH$_2$X, where X is H. Cl, or F and
   Y is H or Cl, in either the vapor or liquid phase.

16. The process of claim 15 wherein said unsaturated compound is selected from the group consisting of propylene, allyl fluoride, allyl chloride, 2,3-dichloro-1-propene, 2-chloropropene, 2chloro-3-fluoro-1-propene, and 1,3,-dichloropropene.

17. The process of claim 16 wherein said unsaturated compound of formula I is selected from the group consisting of propylene, allyl chloride, and 2,3-dichloro-1-propene and said contacting step is conducted in the vapor phase.

18. The process of claim 16 wherein said unsaturated compound is allyl chloride or 2,3-dichloro-1-propene and the contacting step is conducted in the liquid phase.

* * * * *